(12) United States Patent
Bonneau, Jr. et al.

(10) Patent No.: US 6,394,346 B1
(45) Date of Patent: May 28, 2002

(54) CONTACTLESS SMART CARD HIGH PRODUCTION ENCODING MACHINE

(75) Inventors: Walter C. Bonneau, Jr., Escondido; Graham H. Hilton, San Diego; Neal Blodgett, San Diego; Katarzyna Lombardi, San Diego; Richard A. Pearson, San Diego; Gregory E. Miller, San Diego, all of CA (US)

(73) Assignee: Cubic Corporation, San Diego, CA (US)

( * ) Notice: Subject to any disclaimer, the term of this patent is extended or adjusted under 35 U.S.C. 154(b) by 0 days.

(21) Appl. No.: 09/414,055

(22) Filed: Oct. 7, 1999

(51) Int. Cl.[7] .................................................. G06K 5/00
(52) U.S. Cl. ........................ 235/438; 235/380; 235/435
(58) Field of Search ................................ 235/380, 375, 235/435, 437, 438, 439, 440, 444, 492, 449; 324/76.77; 73/847, 848, 849

(56) References Cited

U.S. PATENT DOCUMENTS

| | | | |
|---|---|---|---|
| 4,795,989 A | | 1/1989 | Hart et al. |
| 5,216,361 A | | 6/1993 | Akar et al. |
| 5,241,277 A | | 8/1993 | Kefalas |
| 5,416,423 A | | 5/1995 | De Borde |
| 5,436,971 A | | 7/1995 | Armbrust et al |
| 5,447,072 A | * | 9/1995 | Holung .................... 73/848 |
| 5,455,870 A | | 10/1995 | Sepai et al. |
| 5,513,272 A | * | 4/1996 | Bogosian, Jr. .............. 382/116 |
| 5,773,880 A | | 6/1998 | Ohno |
| 5,821,758 A | | 10/1998 | Jindal |
| 5,841,786 A | | 11/1998 | Keyes |
| 5,959,278 A | * | 9/1999 | Kobayashi et al. ......... 235/449 |
| 6,039,412 A | * | 3/2000 | Kazo et al. ................. 235/437 |
| 6,283,368 B1 | * | 9/2001 | Ormerod et al. ............ 235/380 |

FOREIGN PATENT DOCUMENTS

| | | |
|---|---|---|
| EP | 0 704 819 A1 | 4/1996 |
| FR | 2 647 574 | 11/1990 |
| JP | 58165175 | 9/1983 |
| JP | 59121486 | 7/1984 |
| JP | 06131510 | 5/1994 |
| JP | 6-131510 A | * 5/1994 |
| JP | 2000-131207 A | * 5/2000 |

OTHER PUBLICATIONS

A. Campbell McCracken, Micas, Marconi Instruments, "Smartcards Require Smart Testing", Electronic Engineering, GB, Morgan–Grampian, LTD. London, vol. 69 No. 842, Feb. 1, 1997, pp. 27–28, 31–32.

* cited by examiner

Primary Examiner—Michael G. Lee
Assistant Examiner—Jared J. Fureman
(74) Attorney, Agent, or Firm—Brown Martin Haller & McClain LLP (57) ABSTRACT

An apparatus automatically analyzes and culls-out defective contactless smart cards. Analysis of smart cards may include RF ranging for both near and far ranges, card type decoding for sorting or encoding using a multi-protocol reader, full memory reading and writing, concave and convex card flexing, optical graphics verification of both sides of card, reading and verifying printed serial numbers, and matching encoded serial numbers with printed serial number. The apparatus also provides high speed encoding and initializing of contactless smart cards. Contactless cards moved through machine serially without belts and rollers. The testing and encoding sequence includes bending and flexing the smart cards followed by RF testing. Self-positioning capability provides accurate card positioning over RF antennas.

33 Claims, 3 Drawing Sheets

CONTACTLESS SMART CARD HIGH
PRODUCTION ENCODING MACHINE

BACKGROUND OF THE INVENTION

The present invention relates to an apparatus for testing and encoding contactless smart cards, and more specifically to a machine for automatically testing and encoding a continuous stream of smart cards for mechanical and electrical functionality, durability, visual aspects, initialization and personalization.

Smart cards are being used in an increasingly wide variety of applications. One such application is the use of smart cards to provide credit/debit payment capability for mass transit users. Smart cards have found applications in many other areas including pay phones, health care, banking, identity and access, pay television, gaming, metering and vending. Retail businesses utilize smart cards to encourage return business, such as the use of smart cards to obtain a discount on merchandise or to gain points that are redeemable for cash or merchandise.

Smart cards generally include one or more integrated circuit ("IC") located within the body of the card to receive and store information. The ICs can be read-only or have read/write capability. Reusable smart cards with read/write capability allow users to add time or value to payment-type smart cards, thus avoiding the inconvenience of having to carry currency, or, in the case of mass transit, exact change, for each usage. The smart card will also contain interface means, which will depend on whether the smart card is a contact-type or contactless smart card. Contactless cards will contain an antenna structure for communication with an RF source, and typically include circuitry adapted for deriving operating power from the RF signal.

Regardless of the application of the smart card, the intention is that the user will carry the card with them wherever he or she goes. Further, the smart cards that are used for payment may be expected to contain value for uses for a long period of time. Smart cards containing data, particularly medical information, are expected to be capable of proper function for years. Since these cards are typically carried in a pocket or wallet, they can be subjected to many different stresses, such as bending and flexing, which could potentially render the card non-functional. Thus, lifetime and durability are important considerations in designing and manufacturing a smart card.

During the manufacturing. process for smart cards, batch inspection and testing are performed to ensure that an acceptable percentage of the smart cards are operational. A typical testing method includes sampling smart cards of a production batch to verify read/write capability of the integrated circuits. Manual inspection is performed on the sample batch to verify print quality and other surface features of the smart cards. The testing procedure may also be partially automated. The smart cards are individually sent through a testing apparatus which writes to and reads from each smart card. The card then passes through an inspection station where a visual spot check is performed on the smart card. The process is repeated for each card of a production batch of smart cards.

Such testing procedures are time and labor intensive. Sampling and manual or visual test procedures are limited in effectiveness and present disadvantages of bottlenecks in the production line, particularly around peak production periods. Specifically, the current testing methods are limited in throughput and cannot provide a testing process at production speeds. A further disadvantage of these testing methods is resulting inconsistencies in shipped quality inherent in subjective human inspection. The current testing methods also do not provide a physical integrity test to ensure that the smart cards can withstand the bending and flexing that occurs with everyday use. Thus, for maximum card quality at a lower per-unit cost, and to ensure a reasonable lifetime for the cards, the manufacturer is in need of an automated testing procedure that provides a competitive advantage of accurate and thorough testing of smart cards at production speeds within one integrated testing apparatus.

SUMMARY OF THE INVENTION

It is an advantage of the present invention to provide improved production methods for detecting and accelerating smart card defects including print, lamination, positional correctness of integrated circuit chips, antenna, signature panels and magnetic stripes, as well as the functionality of the integrated circuits.

Another advantage of the present invention to provide automated comprehensive smart card testing of every smart card at full production speeds including physical integrity tests of flexing and bending, and operational tests of read/write verification of each smart card.

Still another advantage of the present invention is to provide automated surface inspection of every smart card of a production run utilizing a fully automated optical testing at high resolution and production speeds.

Yet another advantage is of the present invention is to improve productivity and lower per-unit costs as well as to provide a competitive advantage of faster turnaround times in the production of smart cards by providing a serial testing line that performs a variety of tests simultaneously on a series of smart cards.

It is a further advantage of the present invention to program or encode smart cards with various applications including stored value, personalization data such as serial number, date, time, and picture, and period pass data for periods including daily, weekly, monthly, and yearly. All applications are registered, i.e. database stored, locally or at a central computer system for security and retrieval.

In the exemplary embodiment of the present invention, the contactless smart card ("CSC") high production encoding machine ("HPEM") of the exemplary embodiment is an automated smart card tester and encoder. In the exemplary embodiment, the contactless smart cards are bulk loaded into an automatic feeding magazine and fed into the encoding "backbone" of the HPEM. The backbone of the HPEM is a testing path or line consisting of a series of testing positions for conducting read/write, optical, and structural tests of a continuous line of smart cards. Each card is immediately preceded by a first card and is immediately followed by a third card. Thus, multiple cards are tested simultaneously along the testing path.

In the exemplary embodiment of the present invention, a card is fed into a first testing position from a feeding magazine. The first test position writes a first test data pattern to the smart card. The card is flexed in one direction as it moves around a roller by means of a transport belt. The smart card proceeds into a second test position wherein the test data is read from the card to verify the physical integrity and the functionality of the IC circuits in the smart card. The HPEM then flexes the card a second time in another direction and feeds the card into a third test position. A second test data string is written to the card and/or the card is encoded with a desired application. In the exemplary embodiment, the card is then optically inspected for top surface and bottom surface defects in a fourth and fifth test position, respectively. Shadow illumination is provided during the optical inspection testing process to verify internal features of the contactless smart card including the loop antenna and IC circuits. The card then moves into position for a final read test to verify that the second test data string or application information is correctly stored and is retrieved from memory.

In the exemplary embodiment, the HPEM includes encoding capability for storing a variety of applications on each smart card in accordance with the intended use of each smart card and utilizing an appropriate communication protocol. Encoding is performed at either the final read or write test position, or alternatively, the HPEM includes an additional encoding position in the test path.

Upon completion of the read/write, flexion, and optical testing, each card passes through a printing position. The cards that pass the read/write, flexing, and optical tests are marked to indicate that the card has passed inspection. For example, a color coded dot may indicate a pass or a rejected card. In the exemplary embodiment, rejected cards may be marked with a reason for rejection. The printer of the exemplary embodiment also has the capability to personalize the smart cards, i.e. with a picture ID correlated to information on smart card. Finally, the cards that have passed all of the tests of the test line are stacked in magazines, bins, or blister packs. Rejected cards are sorted into a separate magazine.

Flexing of the cards during the automated test of the exemplary embodiment includes a concave flexion and a convex flexion. The HPEM provides card flexion by forcing the cards around rotating wheels in a belt transport. The flexion test of each card simulates everyday card use. For example, a card that is carried in a wallet undergoes flexing and bending as the user sits and stands. The flexion test ensures that each smart card continues to receive and send information after physical manipulations of each card.

The reading and writing tests of the HPEM are contactless RF communications with each card, i.e., reading and writing to the integrated chip circuit. In the exemplary embodiment, the read and write tests are performed at different ranges. First a functional read/write antenna is used in the automated test to write to a card. The card is flexed, and a second functional read/write antenna reads the test data from the smart card. Following functional read/write testing, long range and short range testing is performed. In an exemplary embodiment of the present invention, a first range antenna, set to long range, writes to the card. The long range write is performed after the card is flexed for a second time. The long range is adjustable from 50 to 100 millimeters. After the write procedure, the card is exposed to illumination for optical testing and inspection of the card surfaces. A second range antenna, set to short range, is then used to read from the card. The short range is adjustable from 5 to 20 millimeters. In an exemplary embodiment of the invention, the long range antenna is adjustable from 50 to 100 mm. The adjustability ranges of the short and long range antennas is dependent upon the requirements of the test system, and the ranges of the exemplary embodiment are illustrative of one embodiment of the invention.

The smart card testing apparatus of the exemplary embodiment provides production rate testing of smart cards by serially feeding the smart cards through the test path. The smart cards move through various testing positions allowing simultaneous read/write, flexing and optical inspection of a continuous line of cards. The transport means includes combinations of the input belt and flexion drive, gravity, friction, and force from adjacent cards. The HPEM of the exemplary embodiment relies upon friction for high accuracy alignment that is achieved between the cards and the RF and optical testing mechanisms. Accurate alignment is required for RF and optical testing. The cards are aligned and self-positioned with respect to the testing positions since each card touches adjacent cards in the line. The last two cards in the testing position line are stopped by a set of pins. When the pins are released the cards moves forward by one testing position. This process allows the motors driving the belts to run continually and not be turned on and off as in prior art systems. Therefore, the speed of the apparatus is increased.

In the exemplary embodiment, all the memory locations of the smart card are changed to "zeros" during the first test data write, and to all "ones" during the second test data write. These test data strings change each of the memory locations from one state to another during the test for the purpose of fully exercising each memory location. Other embodiments may alternate ones and zeros for the first test data string, and then invert the sequence for the second test data string. Testing algorithms of reading and writing to memory are well known in the art, and any appropriate read/write testing method may be applied.

The exemplary embodiment of the present invention performs a variety of optical tests on each smart card. One optical test consists of a comparison to graphics and printing on each card surface to intended images. A second test is a shadow test wherein a light is applied to one side of the card and the shadows produced by the internal chip and antenna loop are observed on the other side of the card utilizing a camera. A typical defect that can be detected by the shadow test is where an antenna loop is too close to the side of the card.

The HPEM of the exemplary embodiment is constructed primarily of plastic in order to reduce interference and "strange" antenna fields within the device that may develop as a result of metallic parts. Since multiple cards are simultaneously RF tested, interference between the smart card readers must be reduced as much as possible.

In the exemplary embodiment of the present invention, the HPEM tracks a defective card by its location in the transport and rejects the card at the end of the assembly by diverting it into a "bad card" bin. A card is easily tracked because the cards enter the test line serially. The exemplary embodiment also utilizes sensors at key positions along the test line to track each smart card and to ensure accurate positioning before a test commences.

An alternate embodiment of the present invention utilizes card serial numbers as an additional means to track and identify each smart card in the test line. The HPEM includes components, such as a bar code readers and/or optical character recognition ("OCR") readers, for reading printed serial numbers on the cards. The printed serial numbers may be correlated to a permanent electronic serial number of the cards or chip set internal to the cards. The cards can be tracked as they proceed through the test sequence of the HPEM and can be sorted in various ways since the controller can keep track of the cards by the serial number. Tracking serial numbers also allows cards of various types and configurations to be tested within one test batch. Once a card enters the test line, specific optical tests, read/write tests, and final sorting are performed on the card depending upon the serial number of the card. This capability is useful in a manufacturing plant that produces multiple types of smart cards.

BRIEF DESCRIPTION OF THE DRAWINGS

Understanding of the present invention will be facilitated by consideration of the following detailed description of preferred embodiments of the present invention taken in conjunction with the accompanying drawings, in which like numerals refer to parts, and in which.

DETAILED DESCRIPTION OF THE PREFERRED EMBODIMENT

Figure 1:
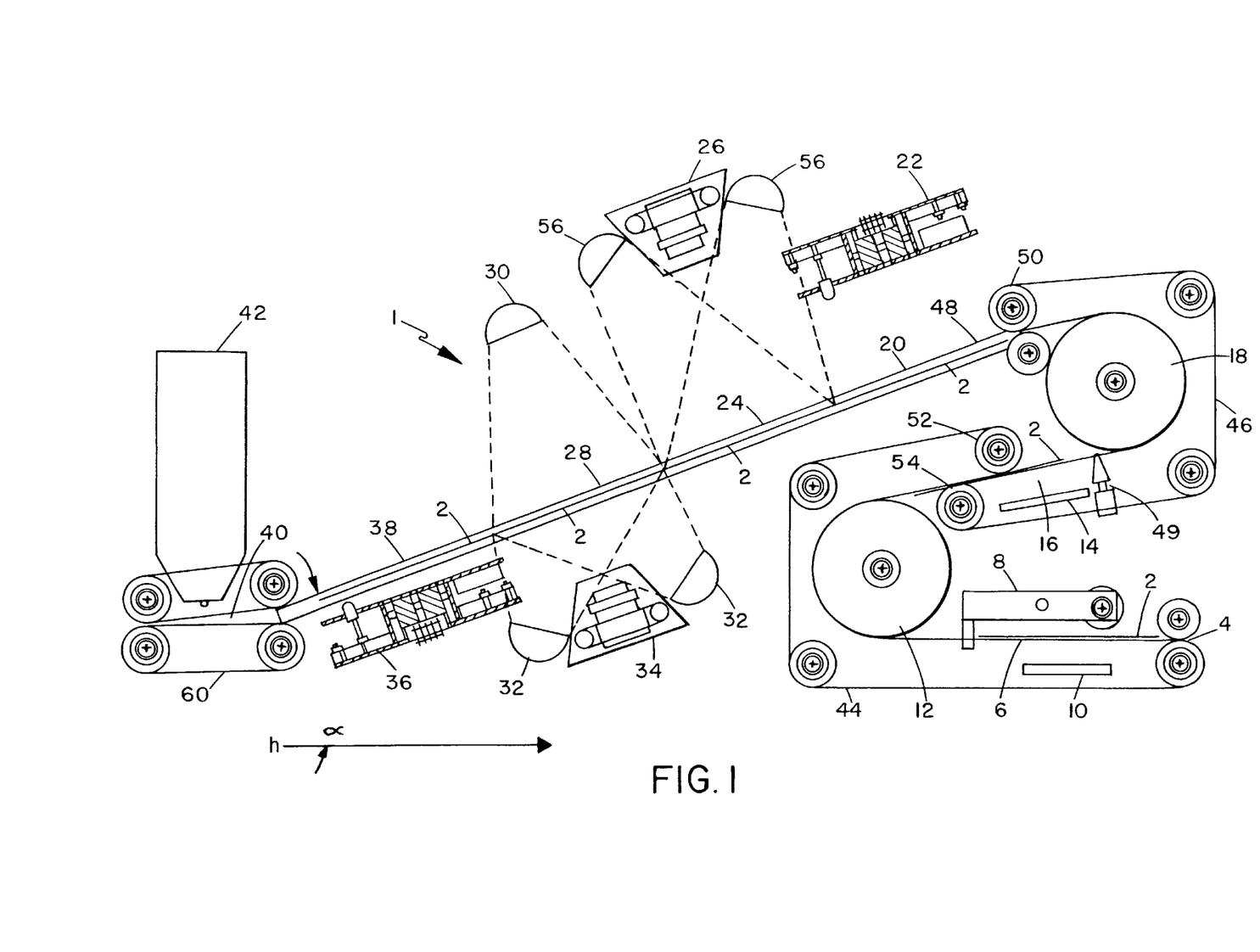
FIG. 1 is an illustration of the smart card testing path of the High Production Encoding Machine contactless card tester.
Figure 2:
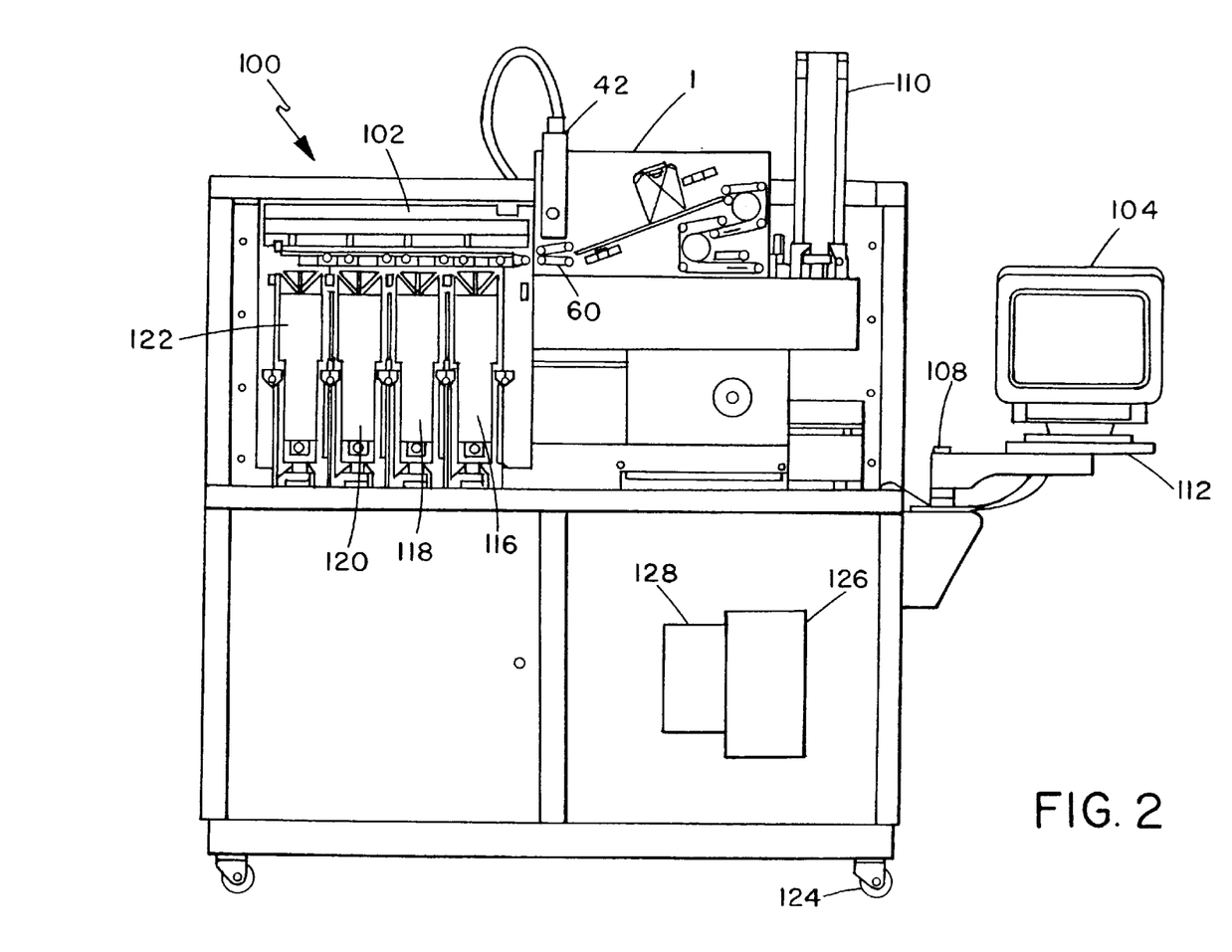
FIG. 2 is a illustration of a portable smart card testing apparatus.

FIG. 1 illustrates the test path or line 1 of a preferred embodiment of the High Production Encoding Machine ("HPEM") for testing and/or encoding contactless smart cards. Smart cards are serially fed into entry rollers 4 from a high-speed card feeder 110 as shown in FIG. 2. Referring back to FIG. 1, a card 2 is fed through the entry rollers 4 to a first position 6. An escrow mechanism 8 maintains the card 2 in the first test position 6 while a first write test is performed. A first functional read/write antenna 10 transmits a bit pattern to the smart card 2 for storage. As the escrow mechanism 8 releases the card 2, a first belt drive 44 moves the smart card 2 around a first flexion roller 12 between the belt 44 and the first flexion roller 12, and a next card is loaded from the feeder 110 into the first position. The first flexion roller 12 flexes the card 2 in a concave manner with respect to a top surface of the card 2. The card 2 continues toward a second test position 16 by moving between a first transport roller 52 and a second transport roller 54 so that transport control of the card 2 switches from the first belt transport 44 to the second belt transport 46.

Figure 3:
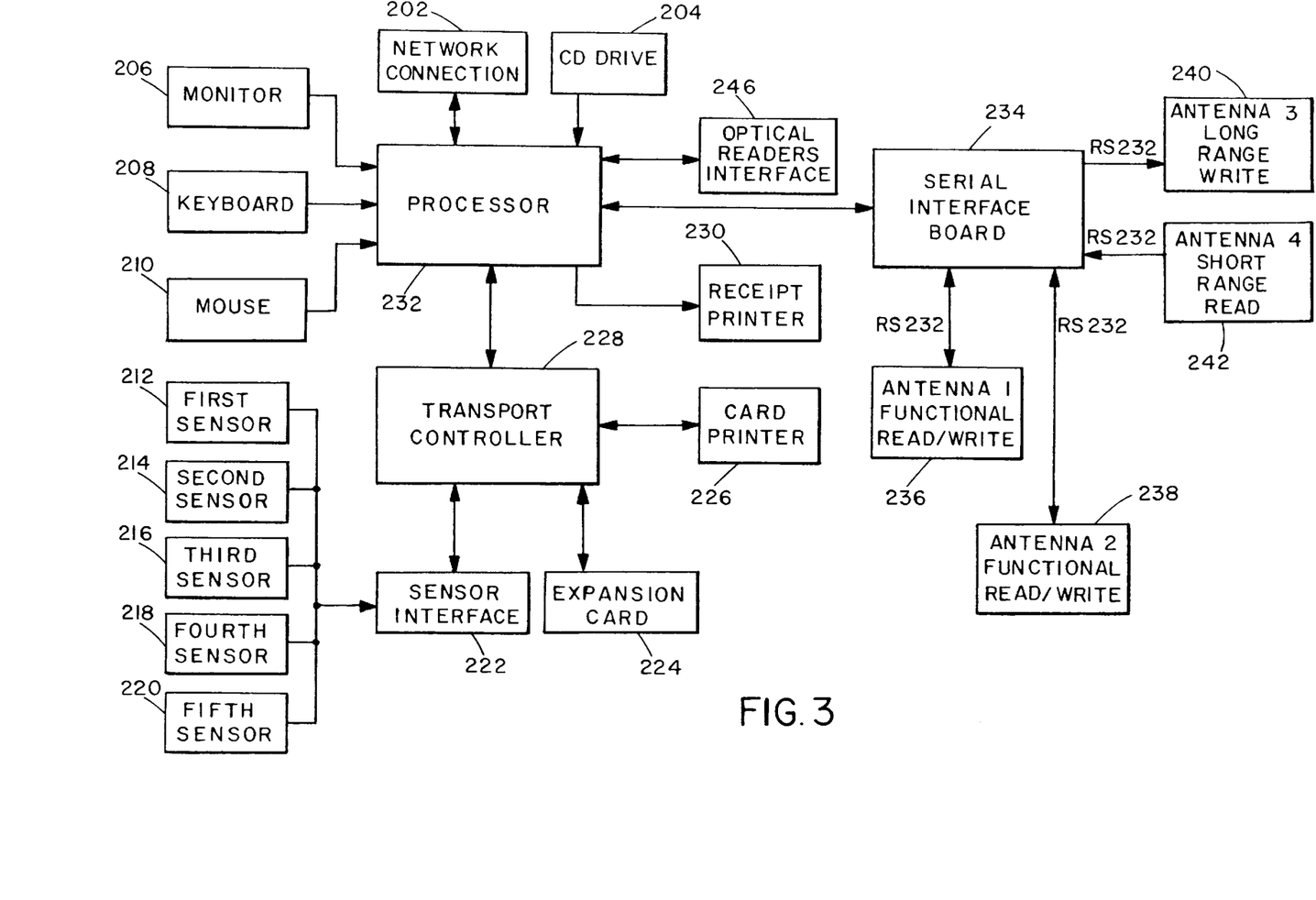
FIG. 3 is a block diagram of the components of a preferred embodiment of the High Production Encoding Machine.

As the smart card moves into the second test position 16, a second escrow mechanism 49 holds the card in the test position. A second functional read/write antenna 14 is utilized to read the bit pattern from the card 2. In the preferred embodiment, the entire memory for each smart card is written to and verified. The functional read/write antennas 10, 14 receive/transmit data that is supplied by a control processor 232 as shown in FIG. 3. Thus, if an error is detected at the read position 16, the processor 232 tracks the location of the card so that the card may be tagged as defective and separated from the error-free cards. Because the movement of the cards are serial, the processor 232 can easily track the position of defective cards through the test line 1. The preferred embodiment of the HPEM also includes line sensors to precisely track the positions of each smart card in the test line.

Referring back to FIG. 1, the card 2 is transported on a second transport belt 46 and is fed around a second flexion roller 18. The card 2 is flexed in an opposite direction, or convex with respect to the top surface of the card 2. The flexion rollers 12, 18 bend each smart card 2 along its length in a convex and concave manner to cull any mechanically weak smart card. The second belt transport 46 includes exit rollers 50 that send the card 2 into a ramp 48 or slide which is sloped downwardly from a point adjacent the exit rollers 50 at an angle a with respect to a horizontal h. Upon entering the ramp 48, the card 2 moves into a third position 20 adjacent a first range antenna 22 set to long range that writes a second test data pattern to the smart card 2. In the preferred embodiment, the second test data pattern is the reverse pattern of the first write to ensure that all memory locations are changed from "0" to "1" or visa versa. Thus, a read and write test is performed at least twice on each smart card 2. The read/write tests exercise all pages of data memory of each smart card by encoding different messages with each write. Movement of the card 2 into the fourth, fifth, and sixth testing positions 24, 28, 38 is achieved through the force of a second following card in the third testing position 20.

The smart cards are moved through the test line 1, one after another in a serial movement. Referring to FIG. 1, once a first card 2 has moved out of the first test position 6, a second card is immediately fed into the first test position 6. Likewise, once the first card 2 moves past the second test position 16, the escrow mechanism 8, under control of the control processor 232, releases the second card in position 1. The transport belt 46 and exit rollers 50 move the first card into a third test position 20, and a third test card is moved into the first test position 6. The first smart card moves past the third test position 20 in the ramp 48 due to the force exerted by the exit rollers 50. The first card is further moved along the shaft as a second card exits from the exit rollers 50. The second card further pushes the first card forward into the fourth test position 24 as it moves into the third test position 20. When the first card is in a sixth test position 38, the second card is in a fifth test position 28, the third card is in a fourth test position 24, and a fourth card is in the third test position 20. This process is repeated for all of the cards to be tested. Thus, the serial movement and adjacent force of the cards provides a means to move the cards through the test line 1 without the use of belts or rollers in the ramp 48. In addition, the serial arrangement of the test line 1 provides continuous operation capability of the HPEM. Continuous operation is particularly useful during peak smart card production periods when production speed testing is required.

Once a first card 2 has received data from the first range antenna 22, the card is optically tested in a fourth position 24. Lamps 56 illuminate the top surface of the card 2. The light is reflected to a high sensitivity linescan camera 26 to ensure accurate image capture at high speeds. A number of high speed image-capturing cameras are known, including CCD and CMOS cameras, and may be used for this purpose. The top surface features and graphics of the smart card 2 are shown on a monitor 104 as shown in FIG. 2. The card graphics are automatically compared with a desired card graphics templates to identify defects. The processor 232 stores a template of a perfect card in memory and compares each inspected card to this template. Print inspection algorithms analyze the card for the highest level of inspection accuracy while allowing for typical process variations. In another embodiment, the card graphics are compared against the desired card graphics by an operator or by a combination of automatic comparison and verification by an operator. Cards that do not have acceptable surface graphics are tracked by the processor 232 as shown in FIG. 3, and are marked as defective by a printer 226. Typical surface features that are verified include print defects, lamination flaws, positional accuracy of magnetic strips, signature panels and holograms.

The bottom surface graphics of the smart card 2 are tested in the fifth test position 28. Lamps 32 illuminated the bottom surface of the card 2 as camera 34 collects the reflected light. The bottom surface image is automatically compared to a template of the bottom surface graphics. A defective card is tracked by the processor 232 as having a defect in bottom surface graphics. The fifth test position 28 also includes a transmissive light test to verify the position of the antenna loop and IC circuits that are internal to each card. A high powered lamp 30 is directed toward the top surface of the card 2. The light allows the camera 34 to "see through" the card 2, or more accurately, the camera 34 is able to detect a shadow image of the internal components of the card 2. As with camera 26, selection of an appropriate camera for capturing the shadow image is within the level of skill in the art. In the preferred embodiment, the shadow image is compared automatically with a template consisting of an expected shadow image. A mismatch is recorded by the processor, and the card is tracked and marked as defective if the mismatch is not within specified tolerances.

Stacking cards in the card feeder 110, as shown in FIG. 2, may result in some cards being stacked up-side-down, wherein "up-side-down" is relative to an arbitrary assignment of one surface of the card as the top surface. In one embodiment, the processor will detect up-side-down cards at the optical test positions. If the image of the card surface does not match the expected top surface image, then the processor will compare the image to the expected bottom surface image. A mismatch of both expected images indicates a defective card. Obviously, RF read/write tests are not affected by an up-side-down card since these tests do not rely on direct contact with the card.

For an embodiment of the invention wherein each card must receive a printed mark on a specific surface of the card, the up-side-down cards must be directed to capture. The smart cards are optically checked to establish a correct orientation to that the printing is applied to the correct side and edge of the card. For example, a reflective sensor scan may be performed on an area of the card that has a predetermined mark printed in a clear area such as on the rear of the card next to a signature strip. Cards that do not match the expected scan are directed to a capture area for card re-testing. If a number of cards in succession are incorrectly oriented, then the HPEM stops and request the operator to inspect the cards in the feed hoper 110, as shown in FIG. 2.

In the preferred embodiment, the ramp 48 is open with narrow edge guides that hold the card in order to allow light from the lamps 30, 32, 56 to illuminate the card. The slide 48 provides an open transport path for optical analysis. This configuration maintains no belts, rollers, or shafts to obscure view. In an alternate embodiment, the ramp 48 has transparent or translucent windows positioned in the fourth test position 24 and the fifth test position 28. The components of the test line, e.g. the ramp 48 and belt transports 44, 46, of the preferred embodiment are constructed of plastic where possible in order to minimize interference and additional antenna fields within the testing line 1. Since multiple smart cards are tested simultaneously using the short and long range RF antennas for read and write testing, the test line design must minimize interference between the smart card readers. Therefore, the design of the preferred embodiment utilizes plastic components and strategic positioning of the antennas 10, 14, 22, 36 in the test line 1.

Upon completion of the optical tests, the smart card 2 moves into a sixth test position 38 adjacent a second range antenna 36 which is set at close range. The second range antenna 36 receives the second test data pattern from the smart card 2. The processor 232 compares the data received from the smart card 2 with the test data that was transmitted to the card 2 by the first range antenna 22 that is set at long range. A detected error is stored by the processor 232, and the defective card is tracked for appropriate marking and sorting.

In the preferred embodiment of the invention, the smart card is encoded with a desired application in accordance with the intended use of the card. Referring to FIG. 1, encoding is performed during the final write position 20 or the final read test position 38. In an alternate embodiment, an additional test position (not shown) is included for encoding each smart card. The preferred embodiment also includes multi-protocol contactless smart card readers to test and encode various types of contactless smart cards on the same device.

The range antennas 22, 36 are adjustable in their positions relative to the distance to the smart card 2 under test. The positioning of the antennas must provide read and write capability as well as RF range testing of the contactless smart card. In a preferred embodiment of the present invention, the short range antenna 36 is adjustable from 5 to 20 millimeters. The long range antenna 22 is adjustable from 50 to 100 millimeters. Obviously, the adjustable ranges of the read/write antennas are determined based upon the requirements of the smart card application and are not limited to the ranges of the preferred embodiment.

Upon completion of the final short range read test in the sixth test position 38, the smart card 2 moves in a print position 40 below a card printer 42. In the preferred embodiment of the present invention, a smart card that passes the tests of the test line 1 is marked with a dot or similar mark in a discrete area of the smart card 2. A rejected card is marked to indicated that it is defective. The printer 42 of the preferred embodiment, under the control of the processor 232, may mark the card with a specific reason for rejection. For example, the card 2 may be marked as "antenna loop" to indicate that the internal antenna loop is defective. An operator can examine the rejected cards to verify whether the tester is correctly detecting defects and whether a particular defect is occurring on an unacceptable percentage of the cards such that an adjustment is required in the card manufacturing process. As shown in the block diagram of FIG. 3, the processor 232 automatically captures valuable defect data from the inspection processes for further analysis that can enhance overall operational productivity. The results of the batch testing can be printed on a receipt printer 230.

An illustration of the High Production Encoding Machine ("HPEM") 100 is shown in FIG. 2. Operation and set-up of the machine 100 is controlled through a monitor 104, keyboard 112, and mouse 108 that are connected to a processor 126 that is enclosed in the HPEM 100. The processor 126 of the preferred embodiment is a personal computer ("PC") utilizing a Pentium 400 MHz processor with 64 MB Random Access Memory ("RAM"), however, any type of controller may be utilized for HPEM control. The preferred embodiment also includes a 32x compact disk ("CD") drive 128 for storing program information including desired card images as well as a 1.44 Floppy Drive and a 6.4 GB Integrated Drive Electronics ("IDE") drive. Obviously, other similar components may be utilized for providing data storage for the HPEM. The monitor 104 of the preferred embodiment of the present invention also provides a user-friendly touch screen capability that allows an operator to set up and control inspection of each card with minimal training.

Cards are stacked in a high-speed card feeder 110. The cards are fed into the test line assembly 1 as shown in detail in FIG. 1. The feeder of the preferred embodiment is adjustable to accept varying thickness of cards. A typical contactless smart card has a thickness of 0.030 inches (0.0762 mm), a length of 3.375 inches (85.73 mm), and a width of 2.125 inches (53.98 mm). A preferred embodiment of the present invention has a capability of reading a serial number or a bar code serial number from each card using an appropriate reader such as a bar code reader or an infrared optical character recognition ("OCR") reader. The serial number reader may be located internal to the test line assembly 1, or alternately, the reader may be located between the card feeder 110 and the test line assembly 1. The use of serial numbers allows the processor to track each card and the errors detected on defective cards. Defective cards are automatically marked by printer 42 according to the specific defect and routed to a reject gate without slowing the inspection of incoming cards.

The use of serial numbers or an analogous card identification systems such as multiple protocol smart card communication devices allow different card types to be tested simultaneously by the HPEM. In a serial number identification system, the serial number of each card alerts the processor to perform the required optical and read/write tests in accordance with the card type. The cards are automatically sorted into separate magazines according to card type. Several protocols are currently in use for smart card communication including the Type A and Type B smart card communication protocols as described in ISO/IEC 14443, "Identification cards—Contactless integrated circuit(s) cards—Proximity cards" available to the public. A third type of smart card communication protocol is in accordance with the description included in International Application Number PCT/US92/08892, titled "Noncontact Automatic Fare Collection System", filed Oct. 19, 1992, and published May 13, 1993 as WO93/09516. The PCT publication is incorporated by reference herein. In an embodiment of the present invention, the HPEM uses an existing test position or includes an additional test position to poll a communication channel by transmitting a plurality of initiation messages using a plurality of smart card communication protocols. The smart card communication device monitors the communication channel for a valid acknowledgment message in accordance with a valid smart card communication protocol for a predetermined wait period. When the valid acknowledgment message is received, the smart card communication device notifies the HPEM of the type of smart card that is present and transfers data to the smart card using the valid smart card protocol. The cards are then tested, encoded and sorted according to the applicable card protocol. A communication device for decoding or encoding smart cards that utilize any of the three communication protocols is disclosed in U.S. Application Ser. No. 09/329,775, of Bonneau et al., incorporated herein by reference.

The smart card exists the test line 1 through printer exit rollers 60 as shown in FIGS. 1 and 2. Referring to FIG. 2, the smart card moves into a card sorter 102 that is controlled by the processor. In the preferred embodiment passing cards are stacked in magazines, or stackers 116, 118, 120 that may also be used to package the cards in blister packs. A typical magazine has a 500-card capacity while a blister pack has a 30-card capacity. In one embodiment of the invention for testing a single cardtype, stacking is continuous in stackers 116, 118, 120 wherein stacking automatically changes to a next empty location when one stacker becomes full. Rejected cards are sorted into magazine 122. For tests of multiple card-types, magazines 116, 118, 120 are used to sort card-types. The magazines 116, 118, 120 that are loaded by the card sorter 102 are usable as input magazines for Automatic Ticket Vending Machines ("TVM"). Similarly, the TVM magazines are usable in the HPEM.

In a preferred embodiment, the cards are carried through the card sorter 102 between two flat belts. Diverter modules are located at four positions between the belts. The first three diverters are active, powered by rotary actuators, and divert cards into one of the first three magazines 116, 118, 120. The fourth diverter is passive and directs all card that reach this position into the fourth stacker 120. Optical sensors are positioned between each stack position for the purpose of monitoring card advancement through each diverter stage. A card that does not arrive at the predicted location causes a signal to be sent to the controller 228 in communication with the processor 232 as shown in FIG. 3, to report an error and to stop the encoding process for analysis of the error.

The apparatus shown in FIG. 2 is an illustration of a typical arrangement of the components of the HPEM of a preferred embodiment that is designed for portability and ease of use. The HPEM sits on wheels 124 and may be easily moved into place in a manufacturing line. However, other embodiments of the HPEM may arrange the machine components in other configurations. For example, the components of the HPEM may be arranged to fit within a cabinet of an existing a manufacturing facility. Likewise, in other embodiments of the invention, the optical, read/write, and flexion tests may be arranged in an alternate order.

FIG. 3 illustrates a block diagram of the components of a preferred embodiment of the present invention. A processor 232 having internal hard drive memory controls the operation of the High Production Encoding Machine. A monitor 206, keyboard 208, and mouse 210 are attachable to the processor 232 for providing operator interfaces for set-up and management of the testing of the contactless smart cards. The monitor 206 may also be a touch screen monitor for use with user-friendly software to provide the operator with touch control of the testing process. In addition, the monitor 232 provides the operator with real-time visual display of defective cards. In a preferred embodiment, the operator interfaces with the HPEM utilizing the monitor 206 and keyboard 208. To initiate the HPEM, the operator enters run data including batch number, encoding date, and run quantity by responding to menu prompts. The monitor displays audit data and status data to the operator. Typical audit data includes the run number, the number of tickets that have entered the ticket transport, the number of tickets that have entered the reject bin, the number of tickets that have successfully processed, and the operator ID number. Status data that is displayed includes malfunctions, the current capacity remaining in the stackers, and the full/empty status of the input hopper.

A CD drive 204 is connected to the processor 232 to provide an additional memory source for HPEM test and set-up data. In an alternate embodiment, the CD drive 204 is used to store test data results of testing runs. A receipt printer 230 is attached to the processor 230 for printing test results or any other printable information of the processor 232 and smart card testing software. An optical reader interface 246 is connected to the processor 232 for automatically comparing images from the optical readers to a template image stored in a processor memory source, such as the CD drive or the processor hard drive.

The processor is also connected to a network via a network connection 202 to allow the processor to communicate with other manufacturing systems. For example, a machine for manufacturing smart cards may download information about a particular production run to the HPEM. The network connection 202 also provides a means for connection to outside phone lines and the Internet for remote site control and/or downloading of information to the HPEM.

The processor 232 sends and receives serial data to the antennas by means of a serial interface board 234. The serial interface board 234 is connected to the antennas through standard RS232 serial bus lines. The processor receives data from a functional read/write antenna 238 and a short range antenna 242, which corresponds to antenna 14 and antenna 36, respectively, of the preferred embodiment shown in FIG. 1. The processor 232 writes data to a functional read/write antenna 236 and a long range antenna 240, shown in FIG. 1 as a first functional read/write antenna 10 and a long range antenna 22. In another embodiment of the invention, the HPEM includes high speed encoding capability where the encoding antenna 240 is used to write initialization or other end-user data to the contactless smart card.

Continuing with FIG. 3, the processor 232 is connected to a transport controller 228 for controlling the test line 1 of the HPEM as shown in FIG. 1. The transport controller is connected to a card printer 226 for marking the tested smart cards as passed or rejected, and for marking serialization data and/or other initialization data. The preferred embodiment utilizes an ink jet printer to mark the smart cards. An expansion card 224 can be added to transport controller 228 for providing additional transport controller functions. For example, the expansion card may be required where the transport controller 228 is used to monitor more than one test line. The transport controller is also connected to a sensor interface 222 which receives signals from sensors 212, 214, 216, 218, 220 located along the test line 1. The sensors ensure highly accurate tracking of smart cards as the cards move through the test line. Referring to FIGS. 1 and 3, in the preferred embodiment, the first sensor 212 is located adjacent the first test position 6. The second sensor 214 alerts the transport controller that the smart card 2 is in the second test position 16. The third sensor 216 indicates that the smart card 2 is approaching test position 3. The fourth sensor 218 is located adjacent the third test position 20. Finally, a fifth sensor 5 indicates that a smart card is entering the printing position 40. The number of sensors may be increased or decreased for alternate embodiments of the invention. For example, additional test positions in the test path 1 may necessitate the use of an additional sensor.

Obviously, other embodiments and modifications of the present invention will occur readily to those of ordinary skill in the art in view of these teachings. Therefore, this invention is to be limited only by the following claims, which include all such other embodiments and modifications when viewed in conjunction with the above specification and accompanying drawings.

We claim:

1. An apparatus for testing a plurality of smart cards, the apparatus comprising:
    a processor for controlling a test of the plurality of smart cards;
    a serial test line having a plurality of test positions, the serial test line controlled by the processor, the plurality of test positions comprising:
        at least one write antenna for writing a first test pattern to each smart card of the plurality of smart cards;
        at least one read antenna for reading the first test pattern from each smart card;
        at least one optical surface reading assembly for comparing a template image with an image of each smart card; and
        at least one flexion means for flexing each smart card, the flexion means providing a mechanical integrity test of each smart card;
    a card input means for feeding the plurality of smart cards into the serial test line; and
    a sorting means for sorting the plurality of smart cards, wherein the sorting means is controllable by the processor.

2. The apparatus as in claim 1, wherein the plurality of smart cards are contactless smart cards.

3. The apparatus as in claim 1, wherein the at least one read antenna and the at least one write antenna comprise:
    at least one functional read/write antenna;
    at least one long range antenna; and
    at least one short range antenna.

4. The apparatus as in claim 3, further comprising a reading range test to ensure field functionality.

5. The apparatus as in claim 3, wherein the at least one long range antenna and the at least one short range antenna are adjustable over a range of distances from the smart card.

6. The apparatus as in claim 5, wherein the range of distances for the at least one short range antenna is 5–20 millimeters, and wherein the range of distances for the at least one long range antenna is 50–100 millimeters.

7. The apparatus as in claim 1, wherein the at least one optical surface reading assembly compares a top surface template image with an image of a top surface of each smart card.

8. The apparatus as in claim 1, wherein the at least one optical surface reading assembly comprises a high intensity lamp for creating a shadow image of internal features of each smart card.

9. The apparatus as in claim 1, further comprising a printing assembly for marking each smart card with reject information or with initialization and personalization data.

10. The apparatus as in claim 1, wherein the at least one flexion means comprises a roller and transport belt assembly, and wherein the transport belt bends a smart card around a portion of the roller.

11. The apparatus as in claim 10, wherein the at least one flexion means bends each smart card in a concave manner with respect to a first surface of each smart card.

12. The apparatus as in claim 11, further comprising a second flexion means for bending each smart card in a convex manner with respect to the first surface of each smart card.

13. The apparatus as in claim 1, further comprising means for communication protocol determination for reading/writing to the plurality of smart cards according to a communication protocol utilized by a smart card of the plurality of smart cards.

14. The apparatus as in claim 1, wherein the at least one write antenna is further utilized to encode each smart card of the plurality of smart cards with a desired application according to an intended use of each smart card.

15. A method for testing a plurality of smart cards; the method comprising the steps of:
    feeding a plurality of smart cards into a test line, each card of the plurality fed serially into the test line;
    writing to each smart card as it moves into a write test position;
    performing a first flexion test by flexing each smart card in a first direction;
    reading from each smart card as it moves into a read test position;
    performing a second flexion test by flexing each smart card in a second direction;
    comparing card surface features of each smart card with a first template;
    illuminating each smart card to create a shadow image of the internal features of the smart card;

comparing the internal features with a second template;

identifying each smart card of the plurality of smart cards as a passing smart card or a rejected smart card; and sorting the plurality of smart cards according to the identification.

16. The method as in claim 15, wherein the steps of writing and reading to each smart card is performed utilizing a first and a second functional read/write radio frequency antenna.

17. The method as in claim 16, further comprising steps of:

writing to each smart card utilizing a long range antenna; and reading from each smart card utilizing a short range antenna.

18. The method as in claim 15, wherein the step of identifying each smart card further comprises the step of printing the identification of the passing smart card or the rejected smart card on each smart card after completion of the testing.

19. The method as in claim 15, further comprising step of sensing movements of each smart card in the test line utilizing a plurality of sensors.

20. The method as in claim 15, wherein the step of reading is performed after either of the first or second flexion test.

21. The method as in claim 15, further comprising the step of encoding each smart card according to the intended use of each smart card.

22. The method as in claim 15, wherein each smart card is a member of a specific card-type, and wherein the step of sorting the plurality of smart cards further comprises the step of sorting each smart card according to the specific card-type.

23. The method as in claim 15, wherein the steps of performing a first and second flexion test by flexing each smart card in a first and second direction comprises the steps of concavely flexing each smart card around a first roller and convexly flexing each smart card around a second roller.

24. The method as in claim 15, further comprising the step of encoding each smart card of the plurality of smart cards with an application of a plurality of applications according to an intended use of each said smart card.

25. The method as in claim 15, further comprising the step of determining a communication protocol utilized by each smart card of the plurality of smart cards, wherein the communication protocol is utilized in the steps of writing to and reading from each smart card.

26. An apparatus for testing function and durability of a smart card comprising:

a computer-controlled serial test line comprising a plurality of stations comprising:

means for moving the smart card through the serial test line;

a first station writing to the smart card;

at least one flexion device for applying a bending force to the smart card;

a second station for reading the smart card;

a third station for writing to the smart card;

at least one fourth station for optically inspecting the smart card;

a fifth station for reading the smart card; and a sixth station for marking the smart card according to test results derived from the second, fourth and fifth test stations.

27. The apparatus of claim 26, wherein the at least one fourth station comprises two optical inspection devices, a first optical inspection device comprising a light source and a first camera for generating an image of the smart card, and a second optical inspection device comprising a backlight source and a second camera for generating a shadow image.

28. The apparatus of claim 26, wherein the at least one flexion device comprises a first flexion roller for flexing the smart card in a first direction, and a second flexion roller for flexing the smart card in a second direction opposite from the first direction.

29. The apparatus of claim 26, wherein the first station and the second station each comprise a functional read/write antenna.

30. The apparatus of claim 26, wherein the third station and fifth station each comprise one of a short range antenna and a long range antenna.

31. The apparatus of claim 26, wherein the means for moving comprises a belt and a plurality of transport rollers.

32. The apparatus as in claim 26, further comprising means for determining a communication protocol utilized by the smart card.

33. The apparatus as in claim 26, wherein the third station for writing to the smart card comprises means for writing an application to the smart card according to an intended use of the smart card.

* * * * *